United States Patent
Kim et al.

(10) Patent No.: US 8,364,262 B2
(45) Date of Patent: *Jan. 29, 2013

(54) TACHYARRHYTHMIA SUDDEN ONSET DETECTION WITH HYSTERESIS

(75) Inventors: Jaeho Kim, Redmond, WA (US); Joseph M. Bocek, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 252 days.

This patent is subject to a terminal disclaimer.

(21) Appl. No.: 12/849,714

(22) Filed: Aug. 3, 2010

(65) Prior Publication Data

US 2010/0298902 A1    Nov. 25, 2010

Related U.S. Application Data

(63) Continuation of application No. 11/301,440, filed on Dec. 13, 2005, now Pat. No. 7,774,062.

(51) Int. Cl.
*A61N 1/00* (2006.01)
(52) U.S. Cl. .................................. 607/14; 600/518
(58) Field of Classification Search .............. 607/14, 607/27, 28; 600/600, 518–519
See application file for complete search history.

(56) References Cited

U.S. PATENT DOCUMENTS

| | | |
|---|---|---|
| 5,379,776 A | 1/1995 | Murphy et al. |
| 6,076,014 A | 6/2000 | Alt |
| 6,190,324 B1 | 2/2001 | Kieval et al. |
| 6,493,579 B1 | 12/2002 | Gilkerson et al. |
| 7,774,062 B2 * | 8/2010 | Kim et al. ................ 607/14 |
| 2004/0088013 A1 | 5/2004 | Stadler et al. |

OTHER PUBLICATIONS

"U.S. Appl. No. 11/301,440, Response filed Dec. 2, 2009 to Non-Final Office Action mailed Aug. 10, 2009", 11 pgs.
"U.S. Appl. No. 11/301,440, Notice of Allowance mailed Mar. 25, 2010", 9 Pgs.
"U.S. Appl. No. 11/301,440, Restriction Requirement mailed Mar. 31, 2009", 8 pgs.
"U.S. Appl. No. 11/301,440, Non-Final Office Action mailed Aug. 10, 2009", 5 pgs.
"U.S. Appl. No. 11/301,440, Response and Preliminary Amendment filed Apr. 30, 2009 to Restriction Requirement mailed Mar. 31, 2009", 10 pgs.
"U.S. Appl. No. 12/552,614, Notice of Allowance mailed Jun. 29, 2012", 5 pgs.
"U.S. Appl. No. 12/552,614, Response filed Jun. 15, 2012 to Non Final Office Action mailed Mar. 15, 2012", 14 pgs.

* cited by examiner

*Primary Examiner* — Mark W Bockelman
(74) *Attorney, Agent, or Firm* — Schwegman Lungberg & Woessner, P.A.

(57) ABSTRACT

This document discusses, among other things, detection of a sudden onset of a tachyarrhythmia. A sudden onset of tachyarrhythmia is determined by monitoring changes in intrinsic ventricular rate, such as by using one or more sensing channels in the ICD. A lowest tachyarrhythmia rate threshold is accompanied by a slightly lower "hysteresis tachyarrhythmia rate threshold." If a sudden onset of tachyarrhythmia is declared, the sudden onset status is not reset by the ventricular rate falling below the lowest tachyarrhythmia rate threshold, but is instead reset by the ventricular rate falling below the slightly lower hysteresis tachyarrhythmia rate threshold.

20 Claims, 5 Drawing Sheets

TACHYARRHYTHMIA SUDDEN ONSET DETECTION WITH HYSTERESIS

CLAIM OF PRIORITY

This application is a continuation of and claims the benefit of priority under 35 U.S.C. §120 to U.S. patent application Ser. No. 11/301,440, filed on Dec. 13, 2005, now issued as U.S. Pat. No. 7,774,062, which is hereby incorporated by reference herein in its entirety.

TECHNICAL FIELD

This document pertains generally to detection of tachyarrhythmia such as tachyarrhythmia sudden onset detection with hysteresis.

BACKGROUND

A current implantable cardioverter-defibrillator (ICD) detects tachyarrhythmia when ventricular rate exceeds a specified tachyarrhythmia rate threshold, and classifies the detection as a sudden onset of tachyarrhythmia if exceeding the specified tachyarrhythmia rate threshold occurs together with a sudden change in ventricular rate.

The performance of such an algorithm can be less than certain. For example, the current method of sudden tachyarrhythmia onset determination may not be appropriate when the ventricular rate increases quickly, but then only gradually increases as it crosses the tachyarrhythmia rate threshold. Such a scenario would not be deemed a sudden onset of tachyarrhythmia by such an algorithm.

Another potentially inappropriate operation of such an algorithm occurs when a sudden onset tachyarrhythmia is detected, and anti-tachyarrhythmia therapy is delivered, but where the delivered anti-tachyarrhythmia therapy fails to convert the ventricular heart rhythm from a tachyarrhythmia to a normal heart rhythm and instead results in slowing the ventricular rate below the tachyarrhythmia rate threshold, followed by a gradual increase back above the tachyarrhythmia detection threshold.

In yet another situation, the ventricular rate quickly exceeds the tachyarrhythmia rate detection threshold in a manner indicative of sudden tachyarrhythmia onset, but no anti-tachyarrhythmia therapy is delivered before the ventricular rate spontaneously briefly slows slightly below the tachyarrhythmia rate threshold (thereby resetting the sudden onset status), and then gradually increases back above the tachyarrhythmia rate threshold. Because the current ICD device resets the sudden onset status when the ventricular rate slows below the tachyarrhythmia rate threshold, the subsequent ventricular rate increase above the tachyarrhythmia rate threshold would not be deemed a sudden onset.

In general, inappropriate determination of sudden tachyarrhythmia onset can result in an inappropriate therapy delivery response, including failure to deliver therapy when needed.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
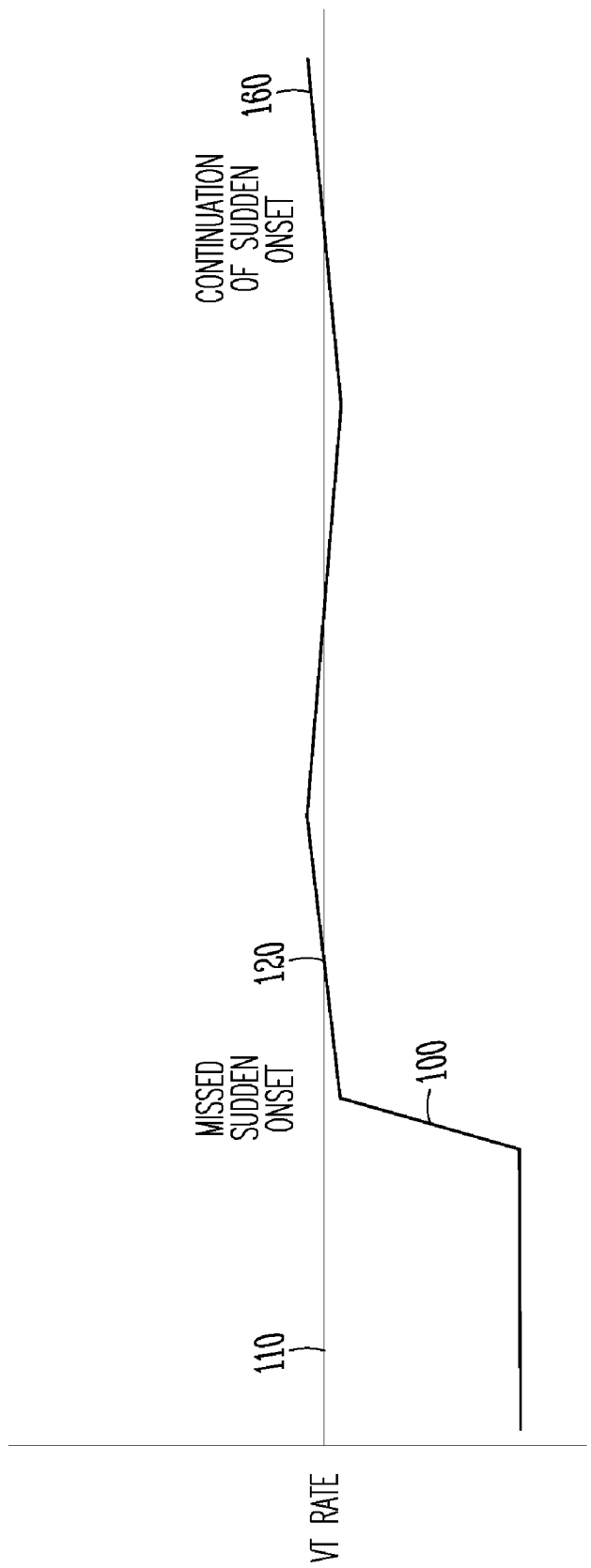
FIG. 1 is a ventricular rate vs. time graph illustrating generally one example of undetected sudden onset of tachyarrhythmia.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The present inventors have recognized, among other things, an unmet need for improved detection of ventricular tachyarrhythmia below the tachyarrhythmia rate threshold and in particular, below a lowest tachyarrhythmia rate threshold in a multi-zone device with multiple different tachyarrhythmia rate thresholds.

A sudden onset of tachyarrhythmia is determined by monitoring changes in intrinsic ventricular rate, such as by using one or more sensing channels in the ICD. A lowest tachyarrhythmia rate threshold is accompanied by a slightly lower "hysteresis tachyarrhythmia rate threshold." If a sudden onset of tachyarrhythmia is declared, the sudden onset status is not reset by the ventricular rate falling below the lowest tachyarrhythmia rate threshold, but is instead reset by the ventricular rate falling below the slightly lower hysteresis tachyarrhythmia rate threshold.

Monitoring typically begins when the intrinsic ventricular rate is below the programmed tachyarrhythmia hysteresis rate threshold. Instructions programmed in memory associated with the ICD's microprocessor control circuitry are used for identifying beat-by-beat intrinsic ventricular rate changes. If the ventricular rate exceeds the tachyarrhythmia rate threshold and then drops below the tachyarrhythmia rate threshold (e.g., as a result of delivering anti-tachyarrhythmia treatment to the heart, or even spontaneously without such therapy delivery), any previously declared sudden onset is maintained—unless the ventricular rate slows below the lower hysteresis tachyarrhythmia rate threshold. When the intrinsic ventricular rate falls below the hysteresis tachyarrhythmia rate threshold, the declared sudden onset status is removed. Otherwise, the previously declared sudden onset condition is maintained.

FIG. 1 is a ventricular rate vs. time graph illustrating generally, an example of undetected sudden onset of tachyarrhythmia in the absence of using a hysteresis tachyarrhythmia rate threshold. In this example, the intrinsic ventricular rate 100 rapidly increases in a manner that would be considered a sudden onset, except for the fact that the ventricular rate change is slower just before crossing the specified ventricular tachyarrhythmia rate threshold 110. Then, the intrinsic ventricular rate continues to increase until just above the tachyarrhythmia rate threshold 110 at 120, but the rate of increase is slow enough to avoid classification as a sudden onset of tachyarrhythmia in a device that performs such a classification only at the tachyarrhythmia rate threshold 110. In this example, the ventricular rate 100 may continue to fluctuate at 160 about the tachyarrhythmia rate threshold 110, without ever triggering a sudden onset classification. As described below, however, where a slightly lower hysteresis tachyarrhythmia rate threshold is used, and sudden onset applies as the intrinsic ventricular rate increases beyond the hysteresis tachyarrhythmia rate threshold, then such sudden onset status will be maintained until the intrinsic ventricular rate drops below such hysteresis tachyarrhythmia rate threshold.

Figure 2:
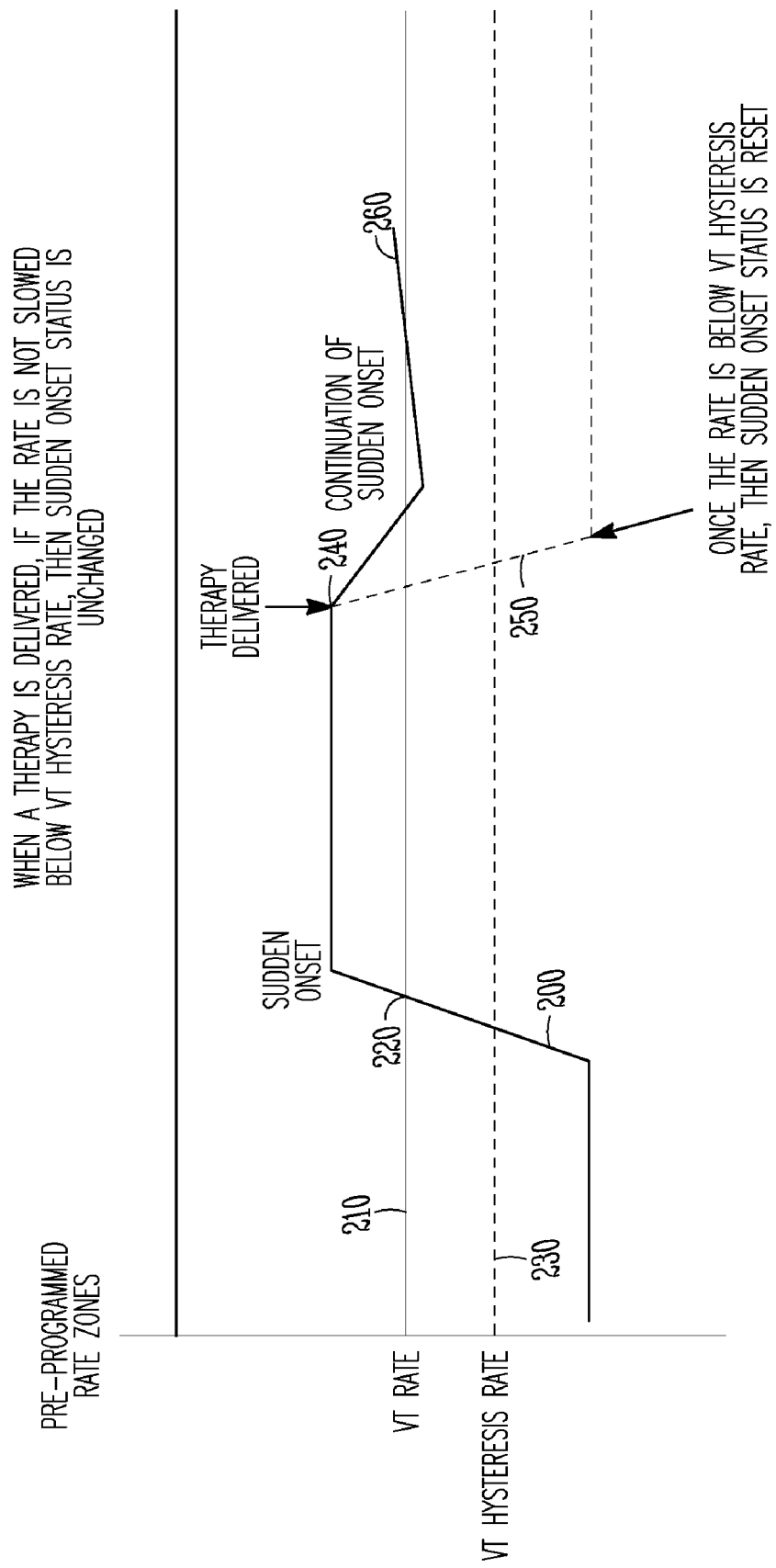
FIG. 2 is a ventricular rate vs. time graph illustrating generally examples of detected sudden tachyarrhythmia onset.

FIG. 2 is a ventricular rate vs. time graph illustrating generally, an example of sudden onset of tachyarrhythmia as detected at a hysteresis tachyarrhythmia rate threshold that is programmed at a slightly lower rate than the tachyarrhythmia rate threshold. In this example, sudden onset of tachyarrhythmia is detected when the intrinsic ventricular rate 200 increases above the hysteresis tachyarrhythmia rate threshold 230, and such rate increase is determined to be sufficiently fast. As an example, when the positive slope of the changing intrinsic ventricular rate exceeds a specified "sudden onset" slope threshold value while at or above the hysteresis tachyarrhythmia rate threshold 230, a sudden onset status is declared—whether or not the intrinsic ventricular rate is above the tachyarrhythmia rate threshold 210. In one example, the hysteresis tachyarrhythmia rate threshold 230 is set to a value that is 90% of the tachyarrhythmia rate threshold 210. In an alternative example, the hysteresis rate threshold 230 is not fixed, but is instead determined dynamically as a function of the rate values observed during a period of rapidly increasing ventricular rate (for example, set at 10% above an average or instantaneous ventricular rate during such a period).

After a sudden onset of tachyarrhythmia is detected, if at 220, the intrinsic ventricular rate 200 then exceeds the tachyarrhythmia rate threshold 210, anti-tachyarrhythmia therapy may be delivered at 240, if the ICD is so programmed. If the anti-tachyarrhythmia therapy is effective at slowing the intrinsic ventricular rate below the hysteresis tachyarrhythmia rate threshold at 250, then the previously-declared sudden onset condition is reset. Otherwise, the sudden onset condition is not reset, and a continuing sudden onset condition at 260 is available for use in a later therapy decision.

Figure 3:
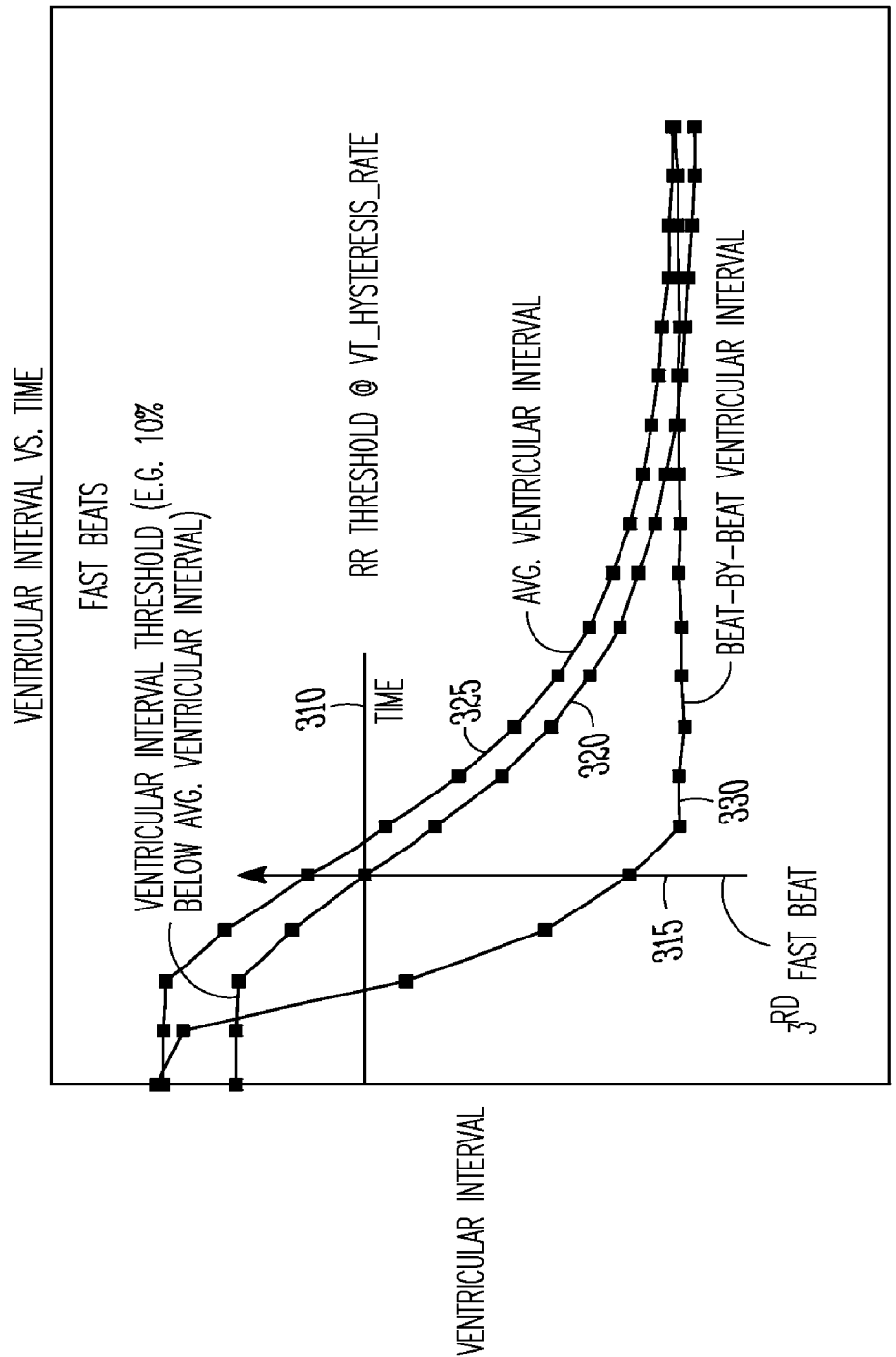
FIG. 3 is a ventricular interval time vs. depolarization instance graph illustrating generally one example of ventricular interval times for consecutive intrinsic ventricular depolarizations.

FIG. 3 is a ventricular rate interval (in milliseconds) vs. time graph showing depolarization instances. The graph of FIG. 3 illustrates generally an example of intrinsic ventricular depolarization interval times measured for consecutive intrinsic ventricular depolarizations. In one example, the hysteresis tachyarrhythmia rate threshold 310 can be set at a fixed value that is 90% of the fixed tachyarrhythmia rate threshold 210, as discussed above. In terms of interval between depolarizations, as shown in FIG. 3, the corresponding hysteresis tachyarrhythmia interval threshold would be set at a fixed value that is 10% longer than the fixed tachyarrhythmia interval threshold.

In another example, as illustrated in FIG. 3, the hysteresis tachyarrhythmia rate threshold 310 is set at a value that is 10% higher (in rate) than a current lowpass filtered or running averaged intrinsic ventricular depolarization rate. This is shown in FIG. 3 in terms of interval between ventricular depolarizations, in which case a corresponding candidate hysteresis tachyarrhythmia interval threshold 320 would be set at a value that is 90% of a current lowpass filtered or running averaged intrinsic ventricular depolarization interval 325, where the current lowpass filtered or running averaged intrinsic ventricular depolarization interval 325 is derived from a beat-by-beat ventricular interval 330.

In the example of FIG. 3, any beat that is at a heart rate exceeding the current lowpass filtered or running averaged intrinsic ventricular depolarization rate by at least 10% is deemed a "fast beat." The occurrence of three consecutive such fast beats at 315 is declared a sudden onset, which, in this example, sets the sudden onset condition, and also dynamically sets an associated hysteresis tachyarrhythmia rate 310 and the value of the candidate hysteresis tachyarrhythmia interval threshold 320 at that third fast beat, which is at 10% (for example) above the then-current lowpass filtered or running averaged intrinsic ventricular depolarization rate (or, viewed in terms of interval instead of rate, at 90% (for example) of the then-current lowpass filtered or running averaged intrinsic ventricular depolarization interval).

In another example, a first candidate hysteresis tachyarrhythmia rate threshold is computed, upon detecting a fixed number of consecutive fast beats, at a fixed percentage above a then-current lowpass filtered or running averaged ventricular rate. A second candidate hysteresis tachyarrhythmia rate threshold is computed at a fixed value below a tachyarrhythmia rate threshold. Then, in a first example, an actual hysteresis tachyarrhythmia rate threshold is chosen by selecting the one of the first and second candidate hysteresis tachyarrhythmia rate thresholds that is at a lower rate. Alternatively, the actual hysteresis tachyarrhythmia rate threshold is selected at a value that is between the first and second candidate hysteresis tachyarrhythmia rate thresholds, such as at a fixed percentage of the difference between the first and second candidate hysteresis tachyarrhythmia rate thresholds.

Figure 4:
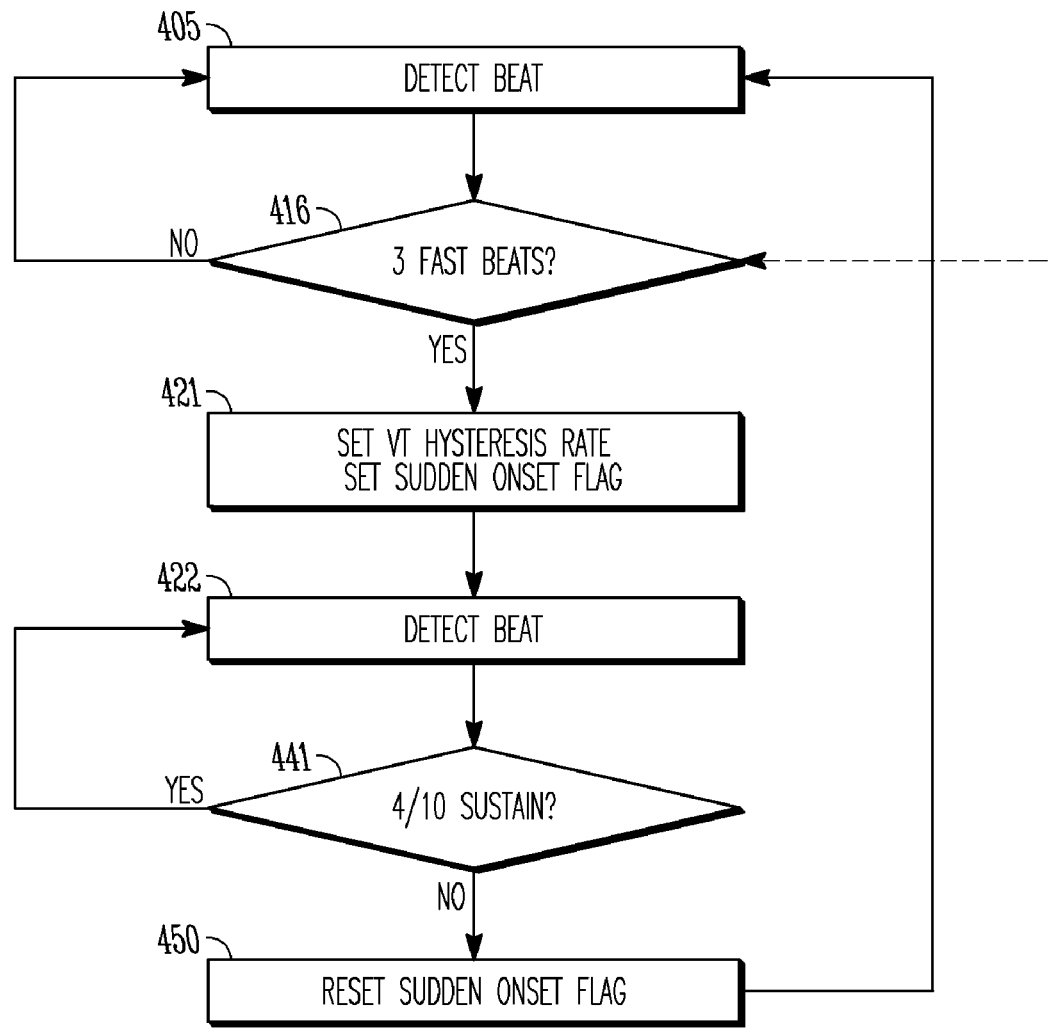
FIG. 4 is a flow chart illustrating generally one implementation of detecting sudden onset of tachyarrhythmia.

FIG. 4 is a flow chart illustrating generally an implementation of a technique for detecting sudden onset of tachyarrhythmia, thereby setting a sudden onset condition flag, and then later resetting the sudden onset condition flag. In this example, at 405, intrinsic ventricular depolarizations are sensed. At 416, if three consecutive fast beats (such as discussed above) are detected, then at 421 a sudden onset condition is declared (thereby setting a sudden onset flag), and the hysteresis tachyarrhythmia rate is dynamically set, such as at 10% above the then-current average ventricular rate, as discussed above. Otherwise, at 416, if three consecutive fast beats are not detected, then process flow returns to 405. In certain examples, the sudden onset determination is then used in a rhythm discrimination algorithm to determine appropriate therapy delivery, such as described in commonly-assigned Gilkerson et al. U.S. Pat. No. 6,493,579 entitled SYSTEM AND METHOD FOR DETECTION ENHANCEMENT PROGRAMMING, which is incorporated by reference herein in its entirety, including its description of using sudden onset information in to perform rhythm discrimination or otherwise determine a need for appropriate therapy.

After setting the sudden onset flag and the hysteresis tachyarrhythmia rate at 421, then at 422 beat detection continues. At 441, if "X" of "Y" (e.g., 4 of 10) beats occur at a rate that falls below the hysteresis tachyarrhythmia rate 310, then the sudden onset condition flag is reset at 450, and process flow returns to 405. Alternatively, at 441, if "X" (e.g., 4) consecutive beats occur at a rate that falls below the hysteresis tachyarrhythmia rate 310, then the sudden onset condition flag is reset at 450, and process flow returns to 405.

In another example, when a sudden onset is declared, but the intrinsic ventricular rate fails to then exceed the tachyarrhythmia rate threshold 210, the episode is potentially of interest as a "slow ventricular tachyarrhythmia" or "slow VT". In that case, a morphology of one or more of the beats of such an episode is compared to a template morphology, such as a stored normal sinus rhythm (NSR) template or a stored supraventricular tachycardia (SVT) template. Such a comparison typically involves computing a correlation coefficient indicating the degree of similarity between the beat morphology and the NSR or SVT template morphology. If there is insufficient similarity between the beat morphology and both of the NSR and SVT template morphologies, then the episode is saved in the ICD memory so that it can be later communicated from the device and reviewed by a physician.

For efficient use of the typically limited ICD memory, it may not be desirable to store multiple slow VT episodes that are similar to each other. Therefore, in certain examples, a new slow VT episode is compared/correlated to a previously-stored slow VT episode. If the correlation exceeds a specified threshold, then the more recent slow VT episode is stored, and the previously-stored slow VT episode is discarded. Similarly, in certain examples, the number and/or duration of stored slow VT episodes is limited (such as to two or three) by one or more programmable or fixed device control parameters.

In another example, if sufficient memory is available, episodes that bear similarity to the SVT template are also stored, although the number and/or duration of such stored SVT episodes can similarly be limited, such as to one or two.

Figure 5:
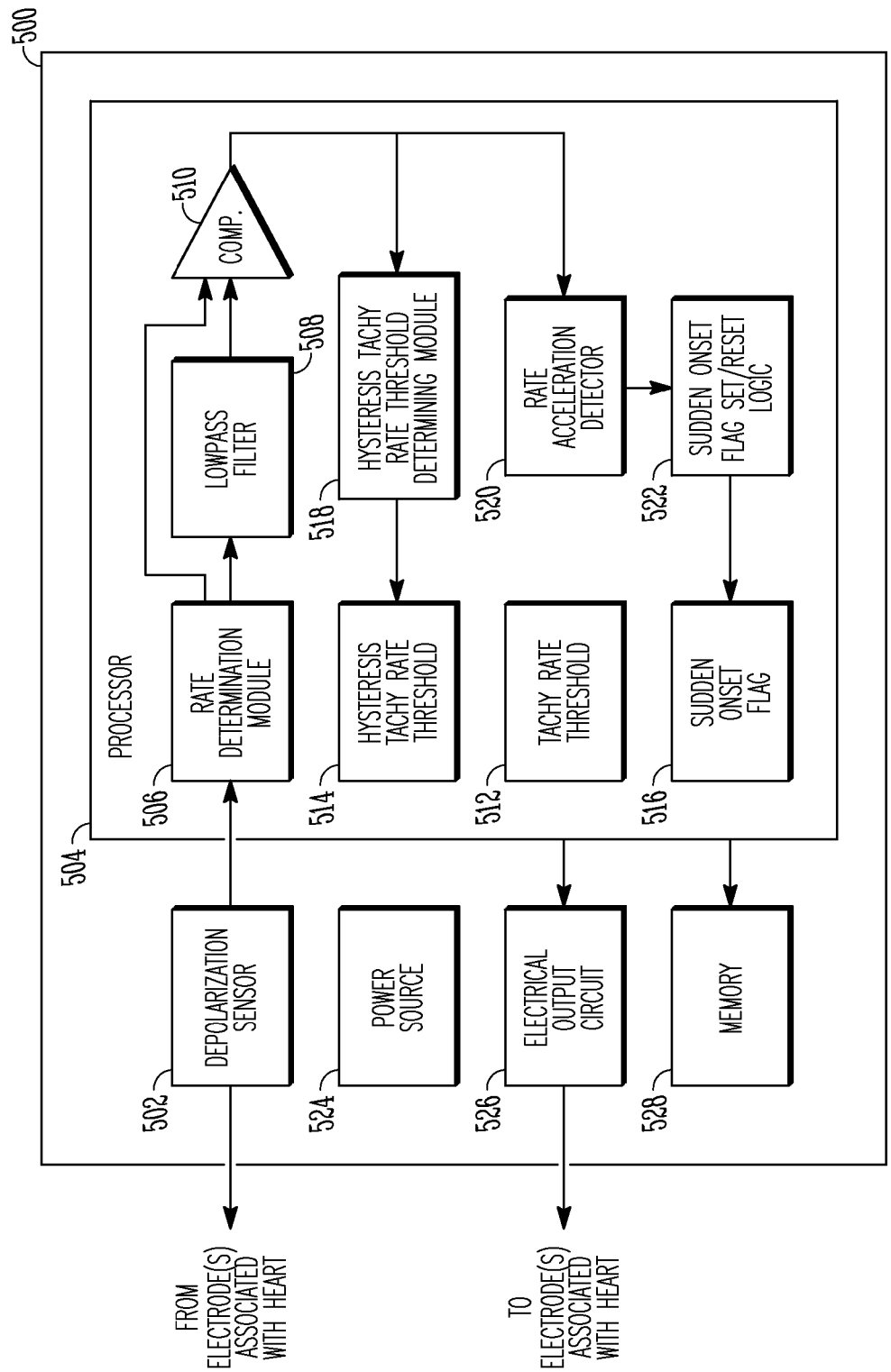
FIG. 5 is a block diagram illustrating generally an example of a cardiac rhythm management device.

FIG. 5 is a block diagram illustrating generally an example of a cardiac rhythm management device 500 for implementing the above methods. In this example, the device 500 includes a depolarization sensor 502 to sense intrinsic ventricular depolarizations corresponding to ventricular heart contractions. A processor 504 receives information from the depolarization sensor 502. The processor 504 includes a rate determination module 506 to determine a ventricular heart rate or corresponding interval between consecutive ventricular depolarizations. An averager or other lowpass filter 508 provides a smoothed indication of ventricular heart rate. A comparator 510 compares the instant heart rate to the smoothed heart rate to determine whether the instant beat is a fast beat, such as described above.

The device 500 includes a tachyarrhythmia rate threshold 512 for making a therapy delivery determination when the ventricular rate exceeds the tachyarrhythmia rate threshold. The device 500 also includes a hysteresis tachyarrhythmia rate threshold 514, for use in making a sudden onset determination, such as described above. A sudden onset flag 516 indicates whether a sudden onset of tachyarrhythmia state exists. A hysteresis tachyarrhythmia rate determining module 518 is used to establish the hysteresis tachyarrhythmia rate threshold 514, such as described above. For example, the hysteresis tachyarrhythmia rate threshold 514 may be set at a fixed value below the tachyarrhythmia rate threshold 512, as described above. Alternatively, the hysteresis tachyarrhythmia rate threshold 514 may be set dynamically based on the smoothed current ventricular rate, as described above. A combination of these two approaches may also be used, as described above. A rate acceleration detector 520 determines whether a sudden onset condition exists, such as described above. Based on this information, a sudden onset flag set/reset logic module 522 sets or resets the sudden onset flag 516, as described above. In the example of FIG. 5, the device 500 also includes a power source 524, an electrical output circuit 526, which is coupled to electrodes associated with the heart for delivering energy thereto, and a memory 528, such as for storing information about episodes, as discussed above.

In the above description and the claims below, certain implementations are described in terms of using a rate between successive cardiac depolarizations, for illustrative clarity. However, alternative implementations that use an interval between successive cardiac depolarizations (instead of the rate) are equivalent, and are often more convenient to implement. Therefore, the above description and below claims should be understood as pertaining to implementations using either rate or intervals.

The above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A method for operating an implantable cardiac rhythm management device, the method comprising:
   determining an intrinsic ventricular rate;
   detecting a sudden increase in the intrinsic ventricular rate;
   setting a sudden onset flag in response to a detection of the sudden increase in the intrinsic ventricular rate;
   delivering an anti-tachyarrhythmia therapy in response to the sudden onset flag being set and the intrinsic ventricular rate exceeding a tachyarrhythmia rate threshold;
   comparing a morphology of one or more heart beats to a template morphology in response to the sudden onset flag being set and the intrinsic ventricular rate not exceeding a tachyarrhythmia rate threshold; and resetting the sudden onset flag in response to the intrinsic ventricular rate falling below a hysteresis tachyarrhythmia rate threshold that is below the tachyarrhythmia rate threshold.

2. The method of claim 1, wherein comparing the morphology of the one or more heart beats to the template morphology comprises comparing the morphology of the one or more heart beats to a stored normal sinus rhythm template.

3. The method of claim 1, wherein comparing the morphology of the one or more heart beats to the template morphology comprises comparing the morphology of the one or more heart beats to a stored supraventricular tachycardia template.

4. The method of claim 1, wherein comparing the morphology of the one or more heart beats to the template morphology comprises computing a correlation coefficient indicating a degree of similarity between the morphology of the one or more heart beats and the template morphology.

5. The method of claim 4, further comprising saving an episode including the one or more heart beats in a memory of the implantable cardiac rhythm management device in response to an insufficient similarity between the morphology of the one or more heart beats and the template morphology being found as an outcome of the comparison between the morphology of the one or more heart beats and the template morphology.

6. The method of claim 1, wherein detecting the sudden increase in the intrinsic ventricular rate comprises detecting a specified number of consecutive fast beats.

7. The method of claim 6, wherein detecting the specified number of consecutive fast beats comprises detecting the specified number of consecutive fast beats comprises detecting beats having a heart rate being at least faster than a lowpass filtered or running averaged ventricular rate by a specified percentage.

8. The method of claim 6, further comprising dynamically establishing the hysteresis tachyarrhythmia rate threshold.

9. The method of claim 1, comprising setting the hysteresis tachyarrhythmia rate threshold to a value that is lower than the tachyarrhythmia rate threshold by a specified value.

10. The method of claim 1, comprising setting the hysteresis tachyarrhythmia rate threshold to a specified percentage of the tachyarrhythmia rate threshold.

11. A method for using an implantable cardiac rhythm management device, the method comprising:
  sensing intrinsic ventricular depolarizations;
  determining an intrinsic ventricular rate between consecutive depolarizations;
  making a therapy delivery determination using the intrinsic ventricular rate and a tachyarrhythmia rate threshold;
  setting a sudden onset flag upon detecting a sudden increase in the intrinsic ventricular rate;
  comparing a morphology of one or more heart beats to a template morphology in response to the sudden onset flag being set and the intrinsic ventricular rate not exceeding the tachyarrhythmia rate threshold;
  establishing a hysteresis tachyarrhythmia rate threshold at a rate that is lower than the tachyarrhythmia rate threshold; and
  resetting the sudden onset flag upon detecting that the ventricular rate has returned below the hysteresis tachyarrhythmia rate threshold.

12. The method of claim 11, wherein detecting the sudden increase in the ventricular rate comprises detecting a fixed number of consecutive fast beats.

13. The method of claim 12, wherein the detecting the fixed number of consecutive fast beats comprises deeming a beat as a fast beat if it occurs at a rate that is at least a fixed percentage faster than a lowpass filtered or running averaged ventricular rate.

14. The method of claim 12, further comprising dynamically establishing the hysteresis tachyarrhythmia rate threshold, upon detecting the fixed number of consecutive fast beats, at a fixed percentage above a then-current lowpass filtered or running averaged ventricular rate.

15. The method of claim 11, wherein the establishing the hysteresis tachyarrhythmia rate threshold comprises establishing the hysteresis tachyarrhythmia rate threshold at a fixed value below a tachyarrhythmia rate threshold.

16. The method of claim 11, comprising:
  computing a first candidate hysteresis tachyarrhythmia rate threshold, upon detecting a fixed number of consecutive fast beats, at a fixed percentage above a lowpass filtered or running averaged intrinsic ventricular rate;
  computing a second candidate hysteresis tachyarrhythmia rate threshold at a fixed value below the tachyarrhythmia rate threshold; and
  choosing an actual hysteresis tachyarrhythmia rate threshold using the first and second candidate hysteresis tachyarrhythmia rate threshold.

17. The method of claim 16, wherein choosing the actual hysteresis tachyarrhythmia rate threshold comprises selecting the one of the first and second candidate hysteresis tachyarrhythmia rate thresholds that is at a lower rate.

18. The method of claim 11, wherein resetting the sudden onset flag upon detecting that the ventricular rate has returned below the hysteresis tachyarrhythmia rate threshold comprises detecting that the ventricular rate has returned below the hysteresis tachyarrhythmia rate threshold when X of Y beats are at a rate that is at or below the hysteresis tachyarrhythmia rate threshold, wherein X and Y are positive integers that are specified such that X is less than or equal to Y.

19. The method of claim 11, wherein resetting the sudden onset flag upon detecting that the ventricular rate has returned below the hysteresis tachyarrhythmia rate threshold comprises detecting that the ventricular rate has returned below the hysteresis tachyarrhythmia rate threshold when X consecutive beats are at a rate that is at or below the hysteresis tachyarrhythmia rate threshold, wherein X is a positive integer.

20. The method of claim 11, wherein comparing the morphology of the one or more heart beats to the template morphology comprises comparing the morphology of the one or more heart beats to a stored normal sinus rhythm template or a stored supraventricular tachycardia template.

* * * * *